United States Patent [19]

Lee et al.

[11] Patent Number: 5,072,047

[45] Date of Patent: Dec. 10, 1991

[54] ORTHO-ALKYLATION OF AROMATIC AMINES

[75] Inventors: Guo-shuh J. Lee, Midland, Mich.; V. Rao Durvasula, Lake Jackson, Tex.; Kirk D. Anderson, Brazoria, Tex.; Louis N. Moreno; Nirad N. Shah, both of Lake Jackson, Tex.

[73] Assignee: The Dow Chemical Company, Midland, Mich.

[21] Appl. No.: 582,446

[22] Filed: Sep. 13, 1990

Related U.S. Application Data

[63] Continuation-in-part of Ser. No. 419,058, Oct. 10, 1989, abandoned.

[51] Int. Cl.$^5$ .............................................. C07C 45/00
[52] U.S. Cl. ...................................... 564/409; 502/231
[58] Field of Search ........................................ 564/409

[56] References Cited

U.S. PATENT DOCUMENTS

| | | | |
|---|---|---|---|
| 2,014,766 | 9/1935 | Isham | 564/409 |
| 2,762,845 | 9/1956 | Stroh et al. | 260/578 |
| 2,814,646 | 11/1957 | Kolka et al. | 260/577 |
| 3,275,690 | 9/1966 | Stroh et al. | 260/576 |
| 3,649,693 | 3/1972 | Napolitano | 260/578 |
| 3,654,331 | 4/1972 | Klopfer | 260/448 R |
| 3,923,892 | 12/1975 | Klopfer | 260/578 |
| 4,128,582 | 12/1978 | Governale et al. | 260/578 |
| 4,219,502 | 8/1980 | Ihrman et al. | 260/578 |
| 4,754,066 | 6/1988 | Buysch et al. | 564/221 |
| 4,760,185 | 7/1988 | Becker | 564/409 |
| 4,973,759 | 11/1990 | Klein et al. | 564/437 |

FOREIGN PATENT DOCUMENTS

| | | | |
|---|---|---|---|
| 560990 | 7/1958 | Canada . | |
| 620573 | 5/1961 | Canada . | |
| 1194890 | 10/1985 | Canada . | |
| 385794 | 4/1973 | Spain . | |
| 823223 | 11/1959 | United Kingdom | 564/409 |

OTHER PUBLICATIONS

Parshall et al., "Homogeneous Catalysis for Agrochemicals, Flavors and Fragrances," *Chemtech*, Jun. 1988, pp. 376–383.

Stroh et al., "Alkylation of Aromatic Amines," *Angew. Chem.* 69, Jahrg. 1957, No. 4, pp. 124–131. (copy of international edition in English attached).

Grant et al., *Grant & Hackh's Chemical Dictionary, Fifth Edition*, p. 118, 1987.

*Primary Examiner*—Glennon H. Hollrah
*Assistant Examiner*—Scott C. Rand

[57] ABSTRACT

A catalytic intermediate useful in the preparation of ortho-alkylated aromatic amines is prepared by heating an amine in the presence of aluminum metal, zinc metal and aluminum chloride. This catalytic intermediate is used to alkylate aromatic amines which may be the same as or different from the amine used in the catalytic intermediate preparation. In a preferred embodiment, toluenediamine is alkylated in the ortho positions to form diethyltoluenediamine.

13 Claims, No Drawings

ORTHO-ALKYLATION OF AROMATIC AMINES

CROSS REFERENCE TO RELATED APPLICATIONS

This application is a continuation-in-part of application, serial number 419,058 filed Oct. 10, 1989, now abandoned.

BACKGROUND OF THE INVENTION

The present invention relates to a process for the alkylation of aromatic amines, particularly the ortho-alkylation of aromatic diamines.

Processes for the preparation of ortho-alkylated aromatic amines from alkenes are known in the art. In one process, aluminum is dissolved in aniline to form aluminum anilide which serves as a catalyst for the alkylation of the aniline or of other aromatic amines. Such a process is taught in U.S. Pat. No. 3,649,693 to Napolitano. Napolitano teaches that the alkylation itself is conducted at significantly elevated temperatures and pressures. Various other references have taught that the addition of mercury chloride, various Friedel Crafts catalysts, iodine or iodine compounds are helpful in improving the efficiency of the reaction.

U.S. Pat. No. 4,760,185 to Becker teaches heating a diamine with an aluminum/zinc alloy and aluminum chloride in the absence of aniline until the evolution of hydrogen is complete. This catalyst mixture is then reacted with a lower alkene at significantly elevated pressure and temperature to form the alkylated phenylenediamine.

The methods known for the ortho-alkylation of aromatic amines require substantially elevated reaction pressures and temperatures; require the presence of environmentally questionable substances such as mercury chloride; require expensive catalysts or require some combination of these factors. Thus what is needed is a method for the ortho-alkylation of aromatic amines which utilizes less expensive, less toxic catalysts and which utilizes relatively mild alkylation conditions.

SUMMARY OF THE INVENTION

The present invention involves a method for the preparation of a catalytic intermediate for the ortho-alkylation of aromatic amines comprising:
(1) heating an amine with
   (a) metallic aluminum;
   (b) aluminum chloride;
   (c) zinc having a particle size ranging from about 20 to about 200 mesh (U.S. standard): and
   (d) optionally, a solvent until the evolution of hydrogen is complete; and the catalyst so prepared.

This invention also involves a process for the ortho-alkylation of aromatic amines wherein all or a portion of the catalytic intermediate prepared as described in the preceding paragraph is contacted with an alkene and optionally, a second aromatic amine which may be the elevated temperatures and pressures under reaction conditions sufficient to produce the desired ortho-alkylated aromatic amines.

The process of the present invention results in the relatively rapid formation of the ortho-alkylated aromatic amines with high yields and selectivities.

The alkylated amines prepared by the process of this invention have a variety of uses. For example, alkylated phenylenediamines prepared by the process of this invention have a broad range of uses including use as antiknock agents in gasoline: as intermediates in the dye industry and as amine extenders in reaction injection molding.

DETAILED DESCRIPTION OF THE ILLUSTRATIVE EMBODIMENTS

Aromatic amines useful in the practice of this invention include those compounds having at least one aromatic ring with at least one amine substituent directly bonded to the aromatic ring or rings.

In one preferred embodiment, aromatic diamines are useful in the preparation of the catalytic intermediate of this invention. Such preferred aromatic diamines correspond to the following formulas:

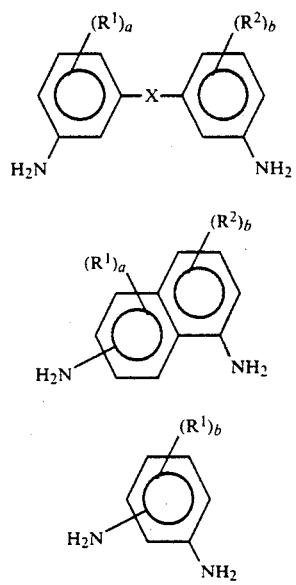

wherein X is a covalent bond, oxygen, sulfur or $-(CR^3R^4)_n-$ wherein $R^3$ and $R^4$ are separately in each occurrence hydrogen or lower alkyl and n is 1 to about 3; $R^1$ and $R^2$ are independently in each occurrence substituted or unsubstituted organic moieties such as alkyl, cycloalkyl and aralkyl moieties; and a and b are independently from zero to three. It is more preferred that $R^1$ and $R^2$ are independently in each occurrence substituted or unsubstituted $C_{1-8}$ organic moieties.

Non-limiting examples of preferred aromatic diamines useful in the catalytic intermediate preparation include phenylenediamines such as m-phenylenediamine itself or substituted m-phenylenediamines. Useful substituents include $C_{1-8}$ organic moieties such as alkyl, cycloalkyl and aralkyl moieties. It is preferred that the substituents are $C_{1-3}$ alkyl groups. Non-limiting examples of useful substituted m-phenylenediamines include 2,4-toluenediamine, 2,6-toluenediamine, 1-ethyl-2,4-phenylenediamine, 1-ethyl-2,6-phenylenediamine, 3,5-diethyl-2,4-toluenediamine, 3,5-diethyl-2,6-toluenediamine, 1-propyl-2,4-phenylenediamine, 1,3-dimethyl-4,6-phenylenediamine, 1-benzyl-2,4-phenylenediamine and mixtures thereof. The use of 2,4-toluenediamine, 2,6-toluenediamine, 3,5-diethyl-2,4-toluenediamine and 3,5-diethyl-2,6-toluenediamine and mixtures thereof is more preferred in the catalytic intermediate preparation process. Aromatic monoamines such as aniline and substituted anilines are also useful in the preparation of the catalytic intermediate of the present invention.

Aluminum metal is useful in the preparation of the catalytic intermediate of this invention. Any size of aluminum particle which will function in the formation of the catalytic intermediate of this invention is useful. It is preferred that particle size not be too small due to problems associated with handling aluminum dust. It is also preferred that particle size not be too large due to the very slow catalytic intermediate formation observed using large particles. It is preferred that the aluminum be used in a mesh size of at least about 20 (U.S. Standard) and no greater than about 200 (U.S. Standard).

Zinc is preferably used in the formation of the catalytic intermediate in the practice of this invention. Various forms of zinc are useful such as metallic zinc powder and dialkyl zinc. Any size of zinc particle which will function in the formation of the catalytic intermediate of this invention is useful. The range of zinc particle sizes useful in the process of this invention generally range from about 20 mesh (U.S. Standard) to about 200 mesh (U.S. Standard). The lower size limit is due, at least in part, to problems associated with handling zinc dust. The upper limit is due to the very slow catalytic intermediate formation observed using large particles. It is preferred that the zinc be used in a mesh size (U.S. Standard) of at least about 50 and no greater than about 150, more preferably at least about 75 and no greater than about 125.

Aluminum chloride is used in the preparation of the catalytic intermediate of the present invention. While it has generally been taught in the art that Freidel Crafts catalytic intermediate are useful in known processes for the formation of aluminum anilide catalytic intermediate systems for the alkylation of aromatic amines, it has surprisingly been found that in the practice of the present invention, aluminum chloride is useful while many other recognized Freidel Crafts catalytic intermediate are not. Other salts, such as zinc chloride have been found to be inoperative in the practice of the present invention. In addition to aluminum chloride, $SnCl_4$, $SiCl_4$ and $ZrI_4$ are useful in the practice of this invention. The use of aluminum chloride is preferred.

The amount of aluminum chloride or other salt used in the preparation of the catalytic intermediate is that which will result in the formation of a catalytic intermediate which will result in the production of the desired alkylated amine. When aluminum chloride is used, it is preferred to use that amount of chloride salt which will result in the ratio of chlorine to aluminum atoms being in the range of about 3:1 to about 1:5; preferably about 2:1 to about 1:2; more preferably about 1.5:1 to about 1:1.5 and most preferably about 1:1.

The catalytic intermediate preparation of the present invention may be conducted neat or a solvent may be used. In some instances, a solvent/reactant may be used. In other instances, a solvent which is inert to the reaction may be used.

For purposes of the present invention, a solvent/reactant is a liquid aromatic amine capable of forming a catalytic intermediate system with aluminum which also acts as a solvent. For example, in one embodiment of the present invention, the aromatic amine used in the preparation of the catalytic intermediate comprises diethyltoluenediamine which is a liquid in which at least some the various components used in catalytic intermediate preparation are soluble and thus acts as a solvent. Without wishing to be bound by any theory, it is believed that a portion of the diethyltoluenediamine present also interacts in some manner with the aluminum and other metals present to form the catalytic intermediate system which is itself soluble in the diethyltoluenediamine. The phrase "catalytic intermediate system" is used to describe the catalytic species that forms from the aromatic amine, aluminum and such other metals as may optionally be present. Non-limiting examples of solvent/reactants useful in the preparation of the catalytic intermediate of this invention include diethyltoluenediamine, aniline and substituted anilines. Inert solvents useful in the process of this invention are those solvents having good solubility for the catalytic intermediate system as described above, aluminum chloride, and aromatic amines and also having good chemical and thermal stability. Such solvents include aromatic ether solvents which may be exemplified by phenoxy biphenyl and diphenyl ether; and alkyl polyaromatic solvents which may be exemplified by terphenyl and diisopropylbiphenyl.

The catalytic intermediate is preferably formed by mixing an amine and solvent in a ratio ranging from about 1:9 to about 9:1 of amine to solvent by weight. It is more preferred that the amine to solvent ratio is greater than about 1:1. Alternatively, the amine is used without a solvent or a solvent/reactant is used. The aluminum is preferably used in an amount such that there are at least about 1 part and no greater than about 10 parts of aluminum per 100 parts of the amine. It is more preferred that there are about 2 to about 6 parts by weight of aluminum per 100 parts by weight of the amine. The zinc is preferably used in an amount to provide at least about 0.05 and no greater than about 10 parts zinc by weight per 100 parts of the amine. It is more preferred that there is about 0.1 to about 2.5 parts by weight of zinc per 100 parts by weight of the amine. Aluminum chloride is preferably used in an amount to provide a chlorine to aluminum atom ratio of about 1:1.

The slurry resulting from the above mixture is heated with the evolution of hydrogen until the metals have dissolved. The completion of catalytic intermediate formation is indicated by the cessation of hydrogen evolution. After venting the hydrogen, the resulting catalytic intermediate is used in the alkylation process in an amount sufficient to provide preferably at least about 1 and no greater than about 10 weight percent metals based on the weight of the amine to be alkylated. Metals in this context refer to the mixture of aluminum and zinc. It is more preferred to use sufficient catalytic intermediate to provide at least about 2 and no greater than about 6 weight percent metals.

The alkylation process of the present invention is useful in the ortho-alkylation of the amine used in the catalytic intermediate preparation and in the ortho-alkylation of amines differing from the amine used in the catalytic intermediate preparation. In the former situation, catalytic intermediate preparation and alkylation may take place in a single reactor without isolation of the catalytic intermediate itself, although separate reactors may be used. In the latter situation, the catalytic intermediate is prepared in one step and may be stored or transported as necessary and then used in a separate alkylation process. For example, toluenediamine may be used in the preparation of the catalytic intermediate and also be the aromatic amine which is alkylated. In contrast, diethyltoluenediamine may be used in the catalytic intermediate preparation and toluenediamine used as the aromatic amine to be alkylated.

As discussed above, the aromatic amine to be alkylated may be the same amine used in the preparation of the catalytic intermediate or may be a different amine. The aromatic amines which may be alkylated by the process of this invention are the same as those used in catalytic intermediate preparation with the exception that the amines to be alkylated are not substituted in the positions ortho to the amine group(s). In a preferred embodiment, toluenediamine is ortho-alkylated to form diethyltoluenediamine.

The alkenes useful in this invention are alkenes containing from two to about eighteen carbon atoms. The alkenes may be unsubstituted or may contain inert substituents and may contain single or multiple unsaturations. It is preferred that the alkenes contain from about two to about twelve carbon atoms and more preferred that they contain from about two to about six carbon atoms. It is most preferred to use alkenes containing from two to about four carbon atoms. Non-limiting examples of alkenes useful in the alkylation reaction of this invention include ethene, propene and butene. It is particularly preferred to use ethene.

One skilled in the art will recognize that both the alkylation reaction and the catalytic intermediate preparation and their combination may be conducted in a batch or continuous manner. As discussed above, the catalytic intermediate preparation may be conducted separately from the alkylation reaction in that the catalytic intermediate is prepared and then stored and/or transported prior to being used in the alkylation reaction. Alternatively, the catalytic intermediate may be prepared, but not isolated or collected prior to being used in the alkylation reaction.

Those skilled in the art will recognize that choice of reactors will depend in part on whether the catalytic intermediate preparation and alkylation reactions take place in the same reactor. The reactor in which the catalytic intermediate is prepared must be designed to withstand hydrogen production and should be free of metals known to be detrimental to the formation of the catalytic intermediate system. An example of such a reactor is a glass-lined reactor. The reactor used in the alkylation process should be inert and capable of withstanding elevated pressures and temperatures. Examples of reactors useful in the alkylation process include those constructed of carbon steel, titanium and zirconium. Clearly, in those processes in which the catalytic intermediate is prepared and the alkylation reaction is conducted in the same reactor will require a reactor which meets the criteria of both.

The choice of conditions useful in the alkylation reaction of the present invention will depend, in part, on the choice of alkene used as an alkylating agent. For example, one skilled in the art will recognize that alkylation pressures and temperatures will vary depending on the alkylating agent. One skilled in the art will also recognize that the choice of other reaction parameters, whether the alkylation reaction should be done in a batch or a continuous manner and similar decisions can be made based on the particular requirements of a given process. It will also be recognized that one skilled in the art understands the dangers of working at high pressures and that selections of temperatures and pressures will be made in accordance with safe engineering practices.

In a preferred embodiment of the invention wherein the alkene used is ethene, preferred temperatures for the ethylation process are at least about 250° C. and no greater than about 350° C. It is more preferred that the ethylation process be operated at temperatures of at least about 270° C. and no greater than about 330° C. Pressures preferred in the ethylation process range from at least about 250 psig up to about 3000 psig, more preferably from at least about 250 psig up to about 1500 psig. Due to the expense of operating high pressure equipment, lower pressures are often preferred commercially. In a particularly preferred embodiment, the alkylation step is conducted at pressures of at least about 250 psig to no greater than about 1000 psig, more preferably no greater than about 700 psig.

The following illustrative examples are provided only to illustrate the invention and should not be interpreted as limiting it in any way. Unless stated otherwise, all parts and percentages are by weight.

Example 1—Preparation of Diethyltoluenediamine

A 150-g portion of 2,4-toluenediamine is heated with 3 g of aluminum powder (40 mesh, U.S. Standard) and 4.5 g of anhydrous aluminum chloride and 1 g of zinc powder (100 mesh, U.S. Standard) to 200° C. with stirring in a 600 cubic centimeter Hastelloy (Hastelloy is a Trademark of Cabot Corporation) C Parr reactor with a glass liner with a mechanical stirrer. Hydrogen begins to evolve at 175° C. and is complete after one hour. The hydrogen is vented. The 600 ml autoclave reactor is then purged with ethene and heated to 300° C. with stirring at a rate of 1500 rpm and ethene pressure of 1000 psi. The uptake of ethene is complete after 0.5 hour and the yield of diethyltoluenediamine is 96 weight percent based on the toluenediamine reacted as determined by gas chromatography.

Example 2—Use of Solvent

The procedure outlined in Example 1 is followed with the exception that 50 g of 4-phenoxybiphenyl are added with an 80:20 weight ratio mixture of 2,4-toluenediamine and 2,6-toluenediamine. The evolution of hydrogen is complete in 0.5 hour and the uptake of ethene is complete in 15 minutes. The yield of diethyltoluenediamine is about 95 weight percent.

Example 3

The procedure outlined in Example 1 is followed with the exception that the solvents identified in Table I below are used. The time for complete conversion of the starting diamines with a selectivity to diethyltoluenediamine of greater than 96 percent is shown in Table I below.

TABLE I

| Run | Solvent (50 g) | Time (Min.) |
| --- | --- | --- |
| 1 | None | 26 |
| 2 | Diphenyloxide | 21 |
| 3 | 4-Phenoxybiphenyl | 18 |

The above data demonstrate that the use of the aromatic ether solvents results in a faster reaction rate than that of a reaction conducted in the absence of such solvents.

Example 4

The general procedure outlined in Example 2 is followed. A 150-g portion of 2,4-toluenediamine is used with 50 g of 4-phenoxybiphenyl as solvent. Three g of aluminum (40 mesh, U.S. Standard), 1 g of zinc (100 mesh, U.S. Standard) and 4.5 g of aluminum chloride are used. The variable in this example is the pressure used in the alkylation step. The time for complete conversion of the starting diamines with a selectivity to diethyltoluenediamine of greater than 96 percent as determined by gas chromatography is shown in Table II below.

TABLE II

| Pressure (psi) | Time (Min.) |
|---|---|
| 1000 | 18 |
| 750 | 35 |
| 500 | 60 |
| 250 | 300 |

The data in the above table demonstrate that reasonable rates for conversion of the phenylenediamine may be obtained at relatively low pressures using the present invention.

Example 5

The procedure outlined in Example 1 is followed using 100 grams of diethyltoluenediamine, 3 grams of aluminum powder (40 mesh, U.S. Standard), 1 gram of zinc (100 mesh, U.S. Standard) and 5 grams of aluminum chloride. The reaction is complete after four hours. The reactor is cooled to room temperature and 150 grams of toluenediamine and 10 grams of 3A molecular sieves (drying agent) is added. The reactor is purged with ethene and heated to 300° C. After about 3.5 hours, the yield of diethyltoluenediamine based on toluenediamine is about 98.3 percent.

Example 6

The procedure outlined in Example 1 is followed using 150 grams of aniline, 2 grams of aluminum powder (40 mesh, U.S. Standard), 0.1 gram of zinc (100 mesh, U.S. Standard) and 5 grams of aluminum chloride. The reaction is complete after one hour. The reactor is purged with ethene and heated to 300° C. After about 3 hours, the yield of 2,6-diethylaniline based on aniline is about 90 percent.

Example 7

An 82-g portion of diethyltoluenediamine is heated with 2.1 g of aluminum powder (40 mesh, U.S. Standard), 2.5 g of anhydrous aluminum chloride and 0.1 g of zinc powder (20 mesh, U.S. Standard) to 300° C. with stirring in a 300 cubic centimeter glass lined pressure reactor with a mechanical stirrer. Hydrogen begins to evolve at 155° C. and is complete after six hours. The hydrogen is vented.

To a 49 g portion of the catalytic intermediate is added 37.5 g of diethyltoluenediamine and 46 g of 2,4-toluenediamine. The reactor is then heated to 300° C. with stirring under an ethene pressure of 965 psig. The conversion of toluenediamine is 100 percent and the selectivity to diethyltoluenediamine based on toluenedi-amine is 80 percent, as determined by gas chromatography.

What is claimed is:

1. A process for the preparation of ortho-alkylated amines comprising preparing a catalytic intermediate by heating a first aromatic amine with
   (1) aluminum:
   (2) aluminum chloride;
   (3) zinc, having a particle size in the range of from about 20 to 200 mesh, U.S. Standard; and
   (4) optionally, a solvent and subsequently reacting the catalytic intermediate with an alkene and, optionally, a second aromatic amine at elevated temperature and pressure under reaction conditions sufficient to produce the ortho-alkylated aromatic amines.

2. The process of claim 1 wherein the first aromatic amine and the second aromatic amine are phenylenediamines.

3. The process of claim 2 wherein the phenylenediamines are selected from the group consisting of toluenediamine, diethyltoluenediamine and mixtures thereof.

4. The process of claim 1 wherein the first aromatic amine and the second aromatic amine are the same.

5. The process of claim 1 wherein the first aromatic amine and the second aromatic are different.

6. The process of claim 1 wherein the alkene contains from about two to about six carbon atoms.

7. The process of claim 6 wherein the alkene is selected from the group consisting of ethene, propene, butene and mixtures thereof.

8. The process of claim 7 wherein the alkene is ethene.

9. The process of claim 1 wherein the reaction of the alkene is carried out at a pressure in the range of about 250 to about 1000 psig.

10. The process of claim 1 wherein the catalytic intermediate preparation and the reaction of the alkene with the catalyst are carried out in different reactors.

11. The process of claim 1 wherein the catalytic intermediate preparation and the reaction of the alkene with the catalyst are carried out in different reactors.

12. The process of claim 11 wherein the catalytic intermediate is prepared in a glass lined reactor and the reaction of the alkene with the catalytic intermediate is carried out in a carbon steel reactor.

13. A process for the preparation of diethyltoluenediamine comprising preparing a catalytic intermediate by heating a first aromatic amine selected from the group consisting of toluenediamine, diethyltoluenediamine and mixtures thereof with
   (1) aluminum;
   (2) aluminum chloride;
   (3) zinc, having a particle size in the range of from about 20 to 200 mesh, U.S. Standard; and
   (4) optionally, a solvent and subsequently reacting the catalytic intermediate with ethene and toluenediamine.

* * * * *

UNITED STATES PATENT AND TRADEMARK OFFICE
CERTIFICATE OF CORRECTION

PATENT NO. : 5,072,047

DATED : December 10, 1991

INVENTOR(S) : Guo-shuh J. Lee, et al

It is certified that error appears in the above-identified patent and that said Letters Patent is hereby corrected as shown below:

Column 8, line 7, "(1) aluminum:", should correctly read --(1) aluminum;--.

Column 8, line 11, "(4) optionally, a solvent and subsequently reacting the" should correctly read --(4) optionally, a solvent and reacting the--.

Column 8, line 57, "(4) optionally, a solvent and subsequently reacting the" should correctly read (4) optionally, a solvent and subsequently reacting the--.

Signed and Sealed this

Sixth Day of July, 1993

Attest:

MICHAEL K. KIRK

*Attesting Officer*       *Acting Commissioner of Patents and Trademarks*